(«12») United States Patent
Riedhauser et al.

(10) Patent No.: US 9,381,507 B2
(45) Date of Patent: Jul. 5, 2016

(54) PROCESS FOR THE PREPARATION OF 4-METHYLPENT-3-EN-1-OL DERIVATIVES

(71) Applicant: Firmenich SA, Geneva 8 (CH)

(72) Inventors: Jean-Jacques Riedhauser, Geneva (CH); Oliver Knopff, Geneva (CH); Luigi Marinoni, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/763,162

(22) PCT Filed: Jan. 21, 2014

(86) PCT No.: PCT/EP2014/051081
§ 371 (c)(1),
(2) Date: Jul. 23, 2015

(87) PCT Pub. No.: WO2014/114615
PCT Pub. Date: Jul. 31, 2014

(65) Prior Publication Data
US 2015/0353463 A1  Dec. 10, 2015

Related U.S. Application Data

(60) Provisional application No. 61/755,711, filed on Jan. 23, 2013.

(51) Int. Cl.
*C07C 51/353* (2006.01)
*C07C 45/67* (2006.01)
*C07C 29/56* (2006.01)
*B01J 31/22* (2006.01)
*B01J 31/24* (2006.01)
*B01J 31/28* (2006.01)
*C07C 67/333* (2006.01)
*C07C 41/48* (2006.01)
*C07C 231/12* (2006.01)

(52) U.S. Cl.
CPC .............. *B01J 31/24* (2013.01); *B01J 31/2291* (2013.01); *B01J 31/28* (2013.01); *C07C 29/56* (2013.01); *C07C 41/48* (2013.01); *C07C 45/67* (2013.01); *C07C 51/353* (2013.01); *C07C 67/333* (2013.01); *C07C 231/12* (2013.01); *B01J 2231/52* (2013.01); *B01J 2531/821* (2013.01)

(58) Field of Classification Search
CPC ........ B01J 31/24; B01J 31/28; B01J 31/2291; B01J 2531/821; B01J 2531/52; C07C 41/48; C07C 231/12; C07C 29/56; C07C 45/67; C07C 67/333; C07C 51/353
See application file for complete search history.

(56) References Cited

U.S. PATENT DOCUMENTS

| 7,132,576 | B2 * | 11/2006 | Haese | B01J 31/1805 502/167 |
| 7,250,536 | B2 | 7/2007 | Jacoby et al. | |
| 8,263,813 | B2 * | 9/2012 | Limbach | C07C 29/56 568/875 |
| 2006/0211889 | A1 * | 9/2006 | Jacoby | B01J 31/146 568/341 |
| 2009/0143585 | A1 * | 6/2009 | Grotjahn | B01J 31/189 546/4 |
| 2010/0099875 | A1 | 4/2010 | Stephan et al. | |
| 2014/0012046 | A1 * | 1/2014 | Heuer | B01J 21/04 568/829 |

FOREIGN PATENT DOCUMENTS

| EP | 1283843 | 3/2006 |
| FR | 2887253 | 12/2006 |
| WO | WO2005061426 | 7/2005 |

OTHER PUBLICATIONS

International Search Report and Written Opinion, application PCT/EP2014/051081, mailed Jun. 20, 2014.
Bauer, Salzer et al., Organometallics 2000, 19, 5471-5476.
Bouachir et al., New Journal of Chem., vol. 11, No. 7, 1987, 527-529.
Cox, et al., J. Chem. Soc., Chem. Commun., 1998, 951-953.
Dodd et al., J. Org. Chem. 1992, 57, 2794-2803.
Ishihara et al., J. Am. Chem. Soc. 2002, 124, 3647-3655.
Stille et al., J. Org. Chem. 1980, 45, 2139-2145.

* cited by examiner

*Primary Examiner* — Shailendra Kumar
(74) *Attorney, Agent, or Firm* — Winston & Strawn LLP

(57) ABSTRACT

The present invention concerns a process for the preparation with high selectivity of a compound of formula (I) by isomerization at room temperature of compound of formula (II) in the presence of a complex of formula [Ru(dienyl)$_2$H]X.

6 Claims, No Drawings

PROCESS FOR THE PREPARATION OF 4-METHYLPENT-3-EN-1-OL DERIVATIVES

TECHNICAL FIELD

The present invention relates to the field of organic synthesis and more specifically it concerns a process for the preparation of 4-methylpent-3-en-1-ol derivatives as defined in formula (I) via an isomerization presenting a good selectivity.

PRIOR ART

Many 4-methylpent-3-en-1-ol derivatives as defined in formula (I) are useful products as such or useful intermediates of the preparation of other important raw materials. The compounds of formula (I), which are poly-isoprenoid derivatives, are of particular interest for the perfumery industry, and in particular 4,8-dimethylnona-3,7-dien-1-ol or 4,8,12-trimethyltrideca-3,7,11-trien-1-ol. The latter compound is described as an important intermediate for the preparation of industrially relevant compounds such as Cetalox® (dodecahydro-3a,6,6,9a-tetramethyl-naphtho[2,1-b]furan; origin: Firmenich SA, Geneva, Switzerland).

The compound of formula (I) 4,8,12-trimethyltrideca-3,7,11-trien-1-ol has been prepared by many different processes, such as reduction of the corresponding carboxylic derivatives (e.g. see K. Ishihara et al in *JACS*, 2002, 3647), or by other exotic methods such as the ones based on boron chemistry (e.g. see D. S. Dodd et al in *JOC*, 1992, 2794). All these methods are complexes or long syntheses and are rarely feasible on an industrial scale.

None of the prior art reports the preparation of a derivative of formula (I) by isomerization of a compound of formula (II), which is in general of easy access.

It is known to this art, from U.S. Pat. No. 7,250,536, to isomerize in a presence of [RuCOD(2-methallyl)$_2$] and BF$_3$.(AcOH)$_2$ (Ru complex and Lewis acid) a disubstituted double bond toward a trisubstituted one. However, the temperature at which the process is carried out at about 100° C. or more suggesting that the catalyst used is not effective on soft conditions required for the kind of substrates described in this application to avoid formation of by-products. Furthermore, this patent is focused on cyclic substrates for which the selectivity issue is less challenging compared to linear ones possibly leading to conjugated products and having several double bonds which could migrate.

The problem of the invention's approach is of reaching a sufficient selectivity in favor of the desired product (see Examples), while having reaction conditions which can be applicable at an industrial scale.

DESCRIPTION OF THE INVENTION

We have now found that the derivatives of formula (I) can be produced in an advantageous manner by means of a new catalytic isomerization allowing a high selectivity and minimal by-products formation.

Therefore, a first object of the present invention is a process for the preparation of a compound of formula (I)

wherein X represents a CHO, CH(OR$^1$)$_2$, COOH, COOR$^2$, CON(R$^3$)$_2$ or a CH$_2$OH group, R$^1$ representing when taken separately a C$_{1-4}$ alkyl or when taken together a C$_{2-8}$ alkanediyl group, R$^2$ representing a C$_{1-5}$ alkyl group, R$^3$ representing when taken separately a C$_{1-4}$ alkyl or when taken together a C$_{3-8}$ alkanediyl group optionally comprising an ether functional group; and R represents a C$_{1-12}$ alkyl or C$_{5-12}$ cycloalkyl group, a C$_{2-12}$ alkenyl or C$_{5-12}$ cycloalkenyl group, or a C$_{6-12}$ alkandienyl or C$_{6-12}$ cycloalkandienyl group;

by the isomerization of the corresponding compound of the formula (II)

wherein R and X have the same meaning as in formula (I); said isomerization being performed in the presence of a complex of formula:

[Ru(dienyl)$_2$H]A   (III)

wherein dienyl represents a C$_5$-C$_{22}$ hydrocarbon group comprising a carbon-carbon double bond and a moiety C=C—C$^-$; and A is a weakly or non-coordinating anion.

For the sake of clarity, it is understood that by the expression "hydrocarbon" it is meant the usual meaning in the art, i.e. a group comprising only carbon or hydrogen atoms and which can be linear, branched or cyclic.

For the sake of clarity, it is understood that by the expression "complex" it is intended a specie which could be a catalyst or a precursor thereof.

According to a particular embodiment of the invention, said X represent a COOH, COOR$^2$ or a CH$_2$OH group, R$^2$ representing a C$_{1-5}$ alkyl group.

According to any one of the above embodiments of the invention, said R is a linear or branched alkyl, alkenyl or non conjugated alkadienyl group. According to any one of the above embodiments of the invention, said R is C$_{2-12}$ group or even a C$_{4-12}$ group.

According to any one of the above embodiments of the invention, said R can be a group of formula

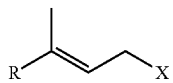

wherein m is 0, 1 or 2. According to any one of the above embodiments of the invention, said m is 1 or 2.

According to any one of the above embodiments of the invention, the compound of formula (I) is 4,8-dimethylnona-3,7-dien-1-ol and the corresponding compound (II) is 8-methyl-4-methylene-non-7-en-1-ol, or the compound of formula (I) is 4,8,12-trimethyltrideca-3,7,11-trien-1-ol and the corresponding compound (II) is 8,12-dimethyl-4-methylene-trideca-7,11-dien-1-ol.

The compounds of formula (II) are known compounds and can be obtained according to the literature.

The compounds (I) and (II) may have one or two carbon-carbon double bonds which can have different stereochemistry (i.e. can be in a E or Z configuration). Each of said carbon-carbon double bond of said compounds, independently from each other, can be in a configuration Z or E or a mixture thereof, or in other worlds each carbon-carbon double bond can be in the form of an essentially pure isomer (i.e. the (3E) when R of compound of formula (I) is the group of formula (i) with m is 0 or 1 or the (3E,7E) when R of compound of formula (I) is the group of formula (i) with m is 2) or in the form of a mixture of isomers, e.g. in the case wherein two carbon-carbon double bonds can have different stereochemistry as with 4,8,12-trimethyltrideca-3,7,11-trien-1-ol a mixture comprising the isomers (3E,7E) and (3Z,7E) in various w/w ratio.

According to any one of the above embodiments of the invention, the starting compound (II) is 8,12-dimethyl-4-methylenetrideca-7,11-dien-1-ol, e.g. in the form of a mixture of isomers of conformation (E) and (Z) wherein the (E) isomer represent at least 50% w/w, or even 80% w/w, or even 90% w/w relative to the total weight of the starting material. In such a case the compound (I) obtained is a mixture of isomers of various double bonds conformation, such as (3E,7E)-4,8,12-trimethyltrideca-3,7,11-trien-1-ol, (3E,7Z)-4,8,12-trimethyltrideca-3,7,11-trien-1-ol and (3Z,7E)-4,8,12-trimethyltrideca-3,7,11-trien-1-ol. According to a particular embodiment of the invention, when compound (I) is 4,8,12-trimethyltrideca-3,7,11-trien-1-ol, said compound is in the form a mixture of the (3E,7E), (3E,7Z), (3Z,7E) and (3Z,7Z) isomers wherein the isomer (3E,7E) represent at least 50% w/w, or even 60% w/w, or even 80% w/w, or even 90% w/w of said mixture.

The invention's process is carried out in the presence of a complex of formula [Ru(dienyl)$_2$H]A.

According to any one of the above embodiments of the invention, said A is a weakly or non coordinative mono anion. In particular said A represents $NO_3^-$, $HSO_4^-$, $BF_4^-$, $PF_6^-$, $SbF_6^-$, $AsF_6^-$, $F^-$ or $R^xSO_3^-$ wherein $R^x$ is a fluoride atom or a $C_{1-8}$ alkyl or $C_{1-10}$ aromatic group optionally substituted by one to three $C_{1-4}$ alkyl group or $C_{1-8}$ fluoroalkylgroup. By fluoroalkyl group it is meant a partially or totally fluorinated alkyl group such $CF_3$.

According to any one of the above embodiments of the invention, said A is a mono anion. In particular said A represents $NO_3^-$, $BF_4^-$, $PF_6^-$, $SbF_6^-$, $AsF_6^-$, $F^-$ or $R^xSO_3^-$ wherein $R^x$ is a fluoride atom or a $C_{1-8}$ alkyl or $C_{1-8}$ fluoroalkyl group.

According to any one of the above embodiments of the invention, said A is a mono anion. In particular said A represents $BF_4^-$, $PF_6^-$, $SbF_6^-$, $AsF_6^-$, $F^-$ or $R^xSO_3^-$ wherein $R^x$ is a fluoride atom or a $CH_3$ or a $CF_3$ or a phenyl or a para-toluyl.

According to any one of the above embodiments of the invention, said A is $BF_4^-$.

According to any one of the above embodiments of the invention, said dienyl is a deprotonated diene, wherein by diene it is meant a $C_5$-$C_{22}$ hydrocarbon group comprising two carbon-carbon double bonds and which is not aromatic. Therefore said "dienyl" comprises a carbon-carbon double bond and a moiety C=C—C$^-$.

According to any one of the above embodiments of the invention, said dienyl, and the diene generating it, is a linear, branched or cyclic group. According to any one of the above embodiments of the invention, said dienyl is a $C_{5-12}$ group.

As non-limiting examples of suitable "dienyl" one may cite compounds such as a cyclooctadienyl, also known as "codyl" (e.g. 1,3- or 1,4- or 1,5-cyclooctadienyl), norbornadienyl, a 2,4-dimethyl-pentadienyl, a 2,3,4-trimethylpenta-1,3-dienyl, a 2,7-dimethyl-octadienyl or a cycloheptadienyl, and the respective diene from which the dienyl is derived are COD (cyclooctadiene) or NBD (norbornadiene), 2,4-dimethyl-1,3-pentadiene, 2,3,4-trimethylpenta-1,3-diene, 2,7-dimethyl-2,6-octadiene or yet cyclohepta-1,4-diene respectively.

According to any one of the above embodiments of the invention, said complex of formula (III) is [Ru(codyl)$_2$H]A, [Ru(cycloheptadienyl)$_2$H]A, [Ru(2,3,4-trimethylpenta-1,3-dienyl)$_2$H]A or [Ru(2,4-dimethyl-pentadienyl)$_2$H]A.

Complexes of formula (III) are known compounds and can be obtained by applying prior art procedures as for example described in FR 2887253, in EP 1283843, in Salzer et al., *OM* 2000, (19),5471 or in Cox and Roulet in Chem. Commun., 1988, 951 or in F. Bouachir et al, *Nouv. J. Chim.*, 1987, 11, 527 or in a combination of said documents. The complex could be formed in situ. Practical examples are shown in the Example section.

The complex can be added into the reaction medium of the invention's process in a large range of concentrations. As non-limiting examples, one can cite as complex concentration values those ranging from 0.01% to 15%, relative to the molar amount of substrate (II). Preferably, the complex concentration will be comprised between 0.2% and 2%. It goes without saying that the optimum concentration of complex will depend, as the person skilled in the art knows, on the nature of the latter, on the nature of the substrate, of the temperature used during the process, as well as the desired time of reaction.

The reaction is preferably carried out under an inert atmosphere, e.g. under $N_2$, Ar or a mixture thereof. According to any one of the above embodiments of the invention, said inert atmosphere may further comprise up to 5% volume/volume of $H_2$.

The reaction can be carried out in the presence or absence of a solvent. When a solvent is required or used for practical reasons, then any solvent current in such reaction type can be used for the purposes of the invention. Non-limiting examples include $C_{6-10}$ aromatic solvents such as benzene or toluene or xylene, $C_{3-9}$ esters such as AcOEt, $C_{1-2}$ chlorinated solvents such as $CH_2Cl_2$ or dichloro ethane, $C_{2-9}$ ethers as tetrafydrofuran, methyl-tetrahydrofuran, dimethoxyethane, diethylether, $C_{2-9}$ alcohol such as methanol, or mixtures thereof. According to any one of the above embodiments of the invention, the preferred solvent is aromatic solvents such as benzene or toluene or xylene, $C_{3-9}$ esters such as AcOEt, $C_{1-2}$ chlorinated solvents such as $CH_2Cl_2$ or dichloro ethane. The choice of the solvent is a function of the nature of the substrate and of the complex and the person skilled in the art is well able to select the solvent most convenient in each case to optimize the reaction.

The temperature at which the isomerization can be carried out is comprised between –20° C. and 95° C. more preferably in the range of between 20° C. and 60° C. Of course, a person skilled in the art is also able to select the preferred temperature as a function of the melting and boiling point of the starting and final products as well as the desired time of reaction or conversion.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in CDCl$_3$ with a 360 MHz or 100 MHz machine for $^1$H or $^{13}$C respectively, the chemical displacements δ are indicated in ppm with respect to TMS as standard, the coupling constants J are expressed in Hz.

The following abbreviations used herein below have the following meaning:
COD: 1,5-cyclooctadiene
Reaction scheme: for the compound wherein R is Et

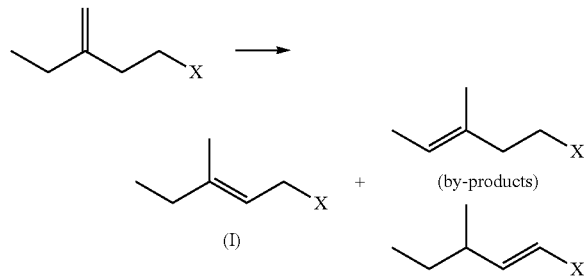

Both product (I) and one of the two by-products have a triply-substituted double bond, fact which renders the selectivity difficult to be achieved. Moreover when X is not an alcohol the double bond of (I) can still migrate to become a much more stable conjugated double bond.

Preparation of the Complexes (III) (in the Form of a Solution)

General Procedure:
Use a precursor of:
Solution Complex (1) ([Ru($\eta^5$-C$_8$H$_{11}$)$_2$H]BF$_4$)
In the glovebox, a Schlenk tube was charged with the [RuCOD(methylallyl)$_2$] complex (0.08 mmol), COD (0.1 ml) and EtOAc (1 ml). After having stirred the mixture for 5 minutes BF$_3$.2CH$_3$COOH (0.035 mmol) was added, to give a slightly yellow solution containing the complex of formula (III).
Solution Complex (2) ([Ru($\eta^5$-C$_8$H$_{11}$)$_2$H]F)
In the glovebox, a Schlenk tube was charged with the [RuCOD(methylallyl)$_2$] complex (0.07 mmol), COD (0.1 ml) and CH$_2$Cl$_2$ (1 ml). After having stirred the mixture for 15 minutes HF (48% in water, 0.138 mmol) was added, to give a slightly yellow solution containing the complex of formula (III).
Solution Complex (3) ([Ru($\eta^5$-C$_8$H$_{11}$)$_2$H]BF$_4$)
In the glovebox, a Schlenk tube was charged with the {Ru($\eta^3$:$\eta^3$-C$_{10}$H$_{16}$)Cl$_2$}$_2$ complex (0.011 mmol), COD (0.1 ml) and CH$_2$Cl$_2$ (2 ml) to give a purple solution. Then the silver tetrafluoroborate (0.058 mmol) was added, forming a suspension. Filtration of the suspension gave a solution containing the complex of formula (III).

Example 1

Catalytic isomerization of (E)-8,12-dimethyl-4-methylenetrideca-7,11-dien-1-ol using Solution Complex (1)

In the glovebox, a Schlenk tube was charged with Solution Complex 1 (1.8 mol % relative to compound (II)) before adding a solution of (E)-8,12-dimethyl-4-methylenetrideca-7,11-dien-1-ol (4.4 mmol) in EtOAc (4 ml). The reaction mixture was stirred 27 hours and then was quenched with aqueous NaOH 1N (0.5 ml) and stirred half an hour. The aqueous layer was decanted, the organic layer dried over anhydrous Na$_2$SO$_4$ and concentrated to give 993 mg of a crude residue. Purification by bulb to bulb distillation afforded 727 mg of a colorless liquid. GLC analysis of this colorless liquid indicated a conversion of 94% and a selectivity toward the formation of (3E,7E)-4,8,12-trimethyltrideca-3,7,11-trien-1-ol superior at 97%.

Example 2

Catalytic isomerization of (E)-8,12-dimethyl-4-methylenetrideca-7,11-dien-1-ol using Solution Complex (3)

In the glovebox, a Schlenk tube was charged with Solution Complex (3) (8.3 mol % relative to compound (II)), as obtained above, and a solution of (E)-8,12-dimethyl-4-methylenetrideca-7,11-dien-1-ol (0.77 mmol) in CH$_2$Cl$_2$ (1 ml).
After 2 hours, the reaction was quenched with aqueous hydroxylamine (0.2 ml)/Florisil® (100 mg)/Na$_2$SO$_4$ (400 mg). The mixture was stirred 1 hour, filtered and concentrated to give 319 mg of a crude residue. Then, the crude was filtered through a small pad of SiO$_2$ to give, after concentration, 150 mg of a transparent liquid. GLC analysis of this liquid indicated a conversion of 95% and a selectivity toward the formation of (3E,7E)-4,8,12-trimethyltrideca-3,7,11-trien-1-ol superior at 97%.

Example 3

Catalytic isomerization of (E)-8,12-dimethyl-4-methylenetrideca-7,11-dien-1-ol using Solution Complex (2)

In the glovebox, a Schlenk tube was charged with Solution Complex (3) (9 mol % relative to compound (II)), CH$_2$Cl$_2$ (1 ml) and the (E)-8,12-dimethyl-4-methylenetrideca-7,11-dien-1-ol (0.831 mmol). The reaction mixture was stirred for 22 hours at room temperature, before being quenched with Ca(OH)$_2$/Florisil®/Na$_2$SO$_4$, filtered and concentrated. GLC analysis of the crude indicated a conversion of 96% and a selectivity toward the formation of (3E,7E)-4,8,12-trimethyltrideca-3,7,11-trien-1-ol of 50%.

Example 4

Catalytic isomerization of (E)-methyl-8,12-dimethyl-4-methylenetrideca-7,11-dienoate using Solution Complex (1)

In the glovebox, a Schlenk tube was charged with Solution Complex (1) (10.3 mol % relative to compound (II)), and a solution of (E)-methyl 8,12-dimethyl-4-methylenetrideca-7,11-dienoate (>99%, 0.677 mmol) in EtOAc (1 ml). The reaction mixture was stirred 8 hours. Then, the reaction was quenched with aqueous hydroxylamine/Florisil®/Na$_2$SO$_4$. Thereafter, the mixture was filtered, concentrated to give 126 mg of a residue. GLC analysis of the crude indicated a conversion of 90% and a selectivity toward the formation of (3E,7E)-methyl-4,8,12-trimethyltrideca-3,7,11-trienoate superior at 99%.

Example 5

Catalytic isomerization of 8-methyl-4-methylenenon-7-enal using Solution Complex (1)

In the glovebox, a Schlenk tube was charged with Solution Complex (1) (5.4 mol % relative to compound (II)), and a solution of 8-methyl-4-methylenenon-7-enal (1.19 mmol) in EtOAc (1 ml). The reaction mixture was stirred 1 hour. Then, the reaction mixture was filtered through a SiO$_2$ pad and concentrated to give 180 mg of a residue. GLC analysis of the crude indicated a conversion of 84% and a selectivity toward the formation of (E)-4,8-dimethylnona-3,7-dienal of 60%. The low selectivity observed in this case is most probably due to some degradation of the homogeranial on the SiO$_2$ pad.

Example 6

Catalytic isomerization of (E)-8,12-dimethyl-4-methylenetrideca-7,11-dien-1-ol using Complex ([Ru($\eta^5$-2,4-dimethyl-pentadienyl)$_2$H]A)

In the glovebox, a solution with the ([Ru($\eta^5$-2,4-dimethyl-pentadienyl)$_2$] (1.75 mg, 6 μmol, 0.24 mol %) in CH$_2$Cl$_2$ (0.5 ml) was added to a mixture of 2,4-dimethylpenta-1,3-diene (17 μl, 12.25 mg) and (E)-8,12-dimethyl-4-methylenetrideca-7,11-dien-1-ol (600 mg, 2.47 mmol) in CH$_2$Cl$_2$ (2.5 ml). This final solution was split into six 4 ml vials each containing CH$_2$Cl$_2$ (1.5 ml). To the thus prepared vials was then added a solution of one of the following acids (see Table 1).

TABLE 1

Isomerization of (E)-8,12-dimethyl-4-methylenetrideca-7,11-dien-1-ol using various acids

| Entry | Acid (mol %) | Time (h) | Conversion (%) | (E)-4,8,12-trimethyltrideca-3,7,11-trien-1-ol (% sel.)[1] |
|---|---|---|---|---|
| 1 | H$_2$SO$_4$ 96% (0.13) | 5 | 87 | 90 |
|   |   | 21 | 98 | 66 |
| 2 | pTsOH (0.25) | 5 | 54 | 97 |
|   |   | 21 | 77 | 99 |
| 3 | HNO$_3$ 60% (0.25) | 5 | 4 | 51 |
|   |   | 21 | 6 | 76 |
| 4 | CH$_3$SO$_3$H (0.25) | 5 | 80 | >99 |
|   |   | 21 | 93 | >99 |
| 5 | CF$_3$SO$_3$H (0.25) | 5 | 95.4 | >99 |
|   |   | 21 | 95.6. | 97.5. |
| 6 | HBF$_4$·Et$_2$O (0.25) | 5 | 96 | >99 |
|   |   | 21 | 96 | 98 |

[1]Product selectivity based on converted starting (E)-8,12-dimethyl-4-methylenetrideca-7,11-dien-1-ol.

Example 7

Catalytic isomerization of (E)-8,12-dimethyl-4-methylenetrideca-7,11-dien-1-ol using Complex (1) ([Ru($\eta^5$-C$_8$H$_{11}$)$_2$H]BF$_4$) in various solvents The same procedure described in Example 1 was repeated. A solution of complex 1 containing 1 mol % (relative to compound (II)) of catalyst was used and the (E)-8,12-dimethyl-4-methylenetrideca-7,11-dien-1-ol was diluted in the appropriate solvent.

In toluene, GLC analysis after 5 h indicated a conversion of 55% and a selectivity toward the formation of (3E,7E)-4,8,12-trimethyltrideca-3,7,11-trien-1-ol of 95%.

In benzene, GLC analysis after 5 h indicated a conversion of 76% and a selectivity toward the formation of (3E,7E)-4,8,12-trimethyltrideca-3,7,11-trien-1-ol of 99%.

If a solution of complex 1 containing 9.7 mol % (relative to compound (II)) of catalyst was used:

In toluene, GLC analysis after 5 h indicated a conversion of 95% and a selectivity toward the formation of (3E,7E)-4,8,12-trimethyltrideca-3,7,11-trien-1-ol of 89%.

In benzene, GLC analysis after 5 h indicated a conversion of 96% and a selectivity toward the formation of (3E, 7E)-4,8,12-trimethyltrideca-3,7,11-trien-1-ol of 76%.

In methyl-tetrahydrofuran, GLC analysis after 5 h indicated a conversion of 94% and a selectivity toward the formation of (3E,7E)-4,8,12-trimethyltrideca-3,7,11-trien-1-ol of 85%.

In ether, GLC analysis after 5 h indicated a conversion of 95% and a selectivity toward the formation of (3E,7E)-4,8,12-trimethyltrideca-3,7,11-trien-1-ol of 93%.

In dimethoxyethane, GLC analysis after 5 h indicated a conversion of 94% and a selectivity toward the formation of (3E,7E)-4,8,12-trimethyltrideca-3,7,11-trien-1-ol of 83%.

In methanol, GLC analysis after 5 h indicated a conversion of 68% and a selectivity toward the formation of (3E, 7E)-4,8,12-trimethyltrideca-3,7,11-trien-1-ol of 86%.

In tetrahydrofuran, GLC analysis after 5 h indicated a conversion of 94% and a selectivity toward the formation of (3E,7E)-4,8,12-trimethyltrideca-3,7,11-trien-1-ol of 87%.

Example 8

Catalytic isomerization of (E)-8,12-dimethyl-4-methylenetrideca-7,11-dien-1-ol using Complex ([Ru($\eta^5$-cycloheptadienyl)$_9$H]BF$_4$)

In the glovebox, a Schlenk tube was charged with [Ru($\eta^5$-cycloheptadienyl)$_2$H]BF$_4$ (21 mg, 0.056 mmol, 6.3 mol %), cyclohepta-1,3-diene (87 mg, 0.9 mmol, 0.1 ml) and CH$_2$Cl$_2$ (1 ml). This solution was added to a solution of (E)-8,12-dimethyl-4-methylenetrideca-7,11-dien-1-ol (0.215 g, 0.9 mmol, 97.5%) in CH$_2$Cl$_2$ (1 ml). The reaction mixture was stirred under Argon at room temperature for 21.5 h. GLC analysis of this reaction mixture indicated a conversion of 92% and a selectivity toward the formation of (3E,7E)-4,8, 12-trimethyltrideca-3,7,11-trien-1-ol superior at 92%.

What is claimed is:

1. A process for the preparation of a compound of formula (I)

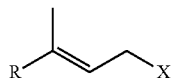

(I)

wherein X represents a CHO, CH(OR$^1$)$_2$, COOH, COOR$^2$, CON(R$^3$)$_2$ or a CH$_2$OH group, R$^1$ representing when taken separately a C$_{1-4}$ alkyl or when taken together a C$_{2-8}$ alkanediyl group, R$^2$ representing a C$_{1-5}$ alkyl group, R$^3$ representing when taken separately a C$_{1-4}$ alkyl or when taken together a C$_{3-8}$ alkanediyl group optionally comprising an ether functional group; and R represents a C$_{1-12}$ alkyl or C$_{5-12}$ cycloalkyl group, a C$_{2-12}$ alkenyl or C$_{5-12}$ cycloalkenyl group, or a C$_{6-12}$ alkandienyl or C$_{6-12}$ cycloalkandienyl group;

by the isomerization of the corresponding compound of the formula (II)

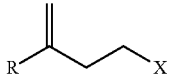
(II)

wherein R and X have the same meaning as in formula (I);

said isomerization being performed in the presence of a complex of formula:

[Ru(dienyl)₂H]A    (III)

wherein dienyl represents a $C_5$-$C_{22}$ hydrocarbon group comprising a carbon-carbon double bond and a moiety C=C—C⁻; and A is a weakly or non-coordinating anion.

2. A process according to claim 1, characterized in that said R is a group of formula

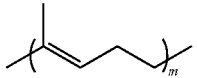
(i)

wherein m is 0, 1 or 2.

3. A process according to claim 1, characterized in that said X represents a $CH_2OH$ group.

4. A process according to claim 1, characterized in that said A represents $NO_3^-$, $HSO_4^-$, $BF_4^-$, $PF_6^-$, $SbF_6^-$, $AsF_6^-$, $F^-$ or $R^xSO_3^-$ wherein $R^x$ is a fluoride atom or a $C_{1-8}$ alkyl or $C_{1-10}$ aromatic group optionally substituted by one to three $C_{1-4}$ alkyl groups or $C_{1-8}$ fluoroalkylgroup.

5. A process according to claim 1, characterized in that said A represents $NO_3^-$, $BF_4^-$, $PF_6^-$, $SbF_6^-$, $AsF_6^-$, $F^-$ or $R^xSO_3^-$ wherein $R^x$ is a fluoride atom or a $C_{1-8}$ alkyl or $C_{1-8}$ fluoroalkylgroup.

6. A process according to claim 1, characterized in that said dienyl is cyclooctadienyl, or norbornadienyl, or 2,4-dimethyl-pentadienyl, or 2,7-dimethyl-octadienyl or cycloheptadienyl or 2,3,4-trimethypenta-1,3-dienyl.

* * * * *